US006475759B1

(12) United States Patent
Carlson et al.

(10) Patent No.: US 6,475,759 B1
(45) Date of Patent: *Nov. 5, 2002

(54) LOW PH LACTIC ACID FERMENTATION

(75) Inventors: Ting Liu Carlson; Eugene Max Peters, Jr., both of Dayton, OH (US)

(73) Assignee: Cargill, Inc., Wayzata, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/949,420

(22) Filed: Oct. 14, 1997

(51) Int. Cl.⁷ .................................................. C12P 7/56

(52) U.S. Cl. ..................... 435/139; 435/170; 435/252.1; 435/252.9

(58) Field of Search ................................ 435/139, 170, 435/252.9, 252.1

(56) References Cited

U.S. PATENT DOCUMENTS

| | | | |
|---|---|---|---|
| 4,142,023 A | | 2/1979 | Bornstein et al. |
| 4,282,323 A | | 8/1981 | Yates |
| 4,698,303 A | | 10/1987 | Bailey et al. |
| 4,769,329 A | * | 9/1988 | Cooper et al. .............. 435/139 |
| 4,771,001 A | | 9/1988 | Bailey et al. |
| 4,963,486 A | | 10/1990 | Hang |
| 5,068,418 A | | 11/1991 | Kulprathipanja et al. |
| 5,068,419 A | | 11/1991 | Kulprathipanja et al. |
| 5,071,754 A | | 12/1991 | Walkup et al. |
| 5,132,456 A | | 7/1992 | King |
| 5,138,074 A | | 8/1992 | Bellis |
| 5,142,023 A | | 8/1992 | Gruber et al. |
| 5,210,296 A | | 5/1993 | Cockrem |
| 5,247,058 A | | 9/1993 | Gruber et al. |
| 5,247,059 A | | 9/1993 | Gruber et al. |
| 5,258,488 A | | 11/1993 | Gruber et al. |
| 5,274,073 A | | 12/1993 | Gruber et al. |
| 5,338,822 A | | 8/1994 | Gruber et al. |
| 5,357,034 A | | 10/1994 | Fridman et al. |
| 5,357,035 A | | 10/1994 | Gruber et al. |
| 5,359,026 A | | 10/1994 | Gruber |
| 5,420,304 A | | 5/1995 | Verser et al. |
| 5,426,219 A | | 6/1995 | Lehnhardt et al. |
| 5,446,123 A | | 8/1995 | Gruber et al. |
| 5,475,080 A | | 12/1995 | Gruber et al. |
| 5,484,881 A | | 1/1996 | Gruber et al. |
| 5,510,526 A | | 4/1996 | Baniel et al. |
| 5,521,278 A | | 5/1996 | O'Brien et al. |
| 5,525,706 A | | 6/1996 | Gruber et al. |
| 5,536,807 A | | 7/1996 | Gruber et al. |
| 5,539,081 A | | 7/1996 | Gruber et al. |
| 5,585,191 A | | 12/1996 | Gruber et al. |
| 5,594,095 A | | 1/1997 | Gruber et al. |
| 5,712,152 A | | 1/1998 | Dequin et al. |
| 5,766,439 A | | 6/1998 | Eyal et al. |
| 5,786,185 A | | 7/1998 | Tsao et al. |

FOREIGN PATENT DOCUMENTS

| | | |
|---|---|---|
| DE | 27 00 644 | 7/1977 |
| EP | 0 076 123 | 4/1983 |
| EP | 0 216 221 A2 | 4/1987 |
| EP | 0 308 064 | 3/1989 |
| EP | 0 614 983 A | 9/1994 |
| GB | 2 251 864 | 7/1992 |
| GB | 2251864 * | 7/1992 |
| WO | WO 85/01064 | 3/1985 |
| WO | WO 93/06226 | 4/1993 |
| WO | WO 95/03268 | 2/1995 |
| WO | WO 95/25081 | 9/1995 |
| WO | WO 95/32301 | 11/1995 |
| WO | WO 97/35489 | 10/1997 |
| WO | WO 98/15517 | 4/1998 |
| WO | WO 98/15519 | 4/1998 |

OTHER PUBLICATIONS

Nakamura, et al., "Microbiology of Corn Fermented with Swine Waste", *Society for Industrial Microbiology*, 19:395–402 (1978).

Roy, et al., "The Application Of Cell Recycle To Continuous Fermentative Lactic Acid Production", *Biotechnology Letters*, 5:665–670 (1983).

Roy, et al., "Lactic Acid Production By *Lactobacillus Delbrueckll* In A Hollow Fiber Fermenter", *Biotechnology Letters*, 4:483–488 (1982).

Stenroos, et al., "Production Of L–Lactic Acid With Immobilized *Lactobacillus DelbrueckII* ", *Biotechnology Letters*, 4:159–164 (1982).

Steiber, et al., "Dialysis Continuous Process for Ammonium Lactate Fermentation: Simulated and Experimental Dialysate—Feed, Immobilized—Cell Systems", *Biotechnology and Bioengineering*, 13:535–549 (1981).

Benthin et al., "Production of Optically Pure D–Lactate by Lactobacillus Bulgaricus and Purification by Crystallisation and Liguid/Liquid Extraction", *Appl Microbiol Biotechnol*, vol. 42, pp. 826–829 (1995).

Davison et al., "A Proposed Biparticle Fluidized–Bed for Lactic Acid Fermentation and Simultaneous Adsorption", *Biotechnology and Bioengineering*, vol. 39, pp. 365–368 (1992).

Fukunishi, Kunio, Chemical Abstracts, vol. 107, No. 1, 1987 "Production of optically active lactic acid" p. 543.

Gonzalez–Vara et al., "Production of L(+)and D(−) Lactic Acid Isomers by Lactobacillus casei subsp. casei DSM 20011 and Lactobacillus coryniformis subsp. torquens DSM 20004 in Continuous Fermentation", *Journal of Fermentation and Bioengineering*, vol. 81, No. 6, pp. 548–552 (1996).

(List continued on next page.)

*Primary Examiner*—Irene Marx
(74) *Attorney, Agent, or Firm*—Merchant & Gould P.C.

(57) ABSTRACT

A process for producing lactic acid which includes incubating acid-tolerant homolactic bacteria in nutrient medium to produce a fermentation broth with high levels of free lactic acid is provided. An isolated acid-tolerant homolactic bacteria capable of producing high levels of free lactic acid is also provided.

17 Claims, 6 Drawing Sheets

OTHER PUBLICATIONS

Nakahara, Tadaatsu, et al., Chemical Abstracts, vol. 118, No. 5, 1993 "Manufacture of D–lactic acid from 1,2–propanediol with Pseudomonas", p. 559.

San–Martin, M. et al., "Liquid–Liquid Extraction of Lactic Acid with Alamine 336", *Journal of Chemical Technology and Biotechnology*, vol. 65, No. 3; Mar. 1, 1996; pp. 281–285.

Stanbury et al. "Principles of Fermentation Technology", 1984, Pergamon Press, pp. 33–37.*

Cann, I., et al., "Characterization of Two Novel Saccharolytic Aerotolerant Thermophiles, *Thermobacter polysaccharolyticum* gen. nov., sp. nov. and *Thermobacter zeae* gen. nov., sp. nov.", Department of Animal Sciences, University of Illinois at Urbana–Champaign, Urbana, IL 61801; 20 pages (undated).

Cheng, P., et al., "Lactic Acid Production from Enzyme–thinned Corn Starch Using *Lactobacillus amylovorus*", *Journal of Industrial Microbiology*, 7:27–34 (1991).

Dequin, S., et al., "Mixed Lactic Acid–Alcoholic Fermentation by *Saccharomyes cerevisiae* Expressing the *Lactobacillus casei* L(+)–LDH", *Bio/Technology*, 12:173–177 (Feb. 1994).

Mehaia, M., et al., "Lactic Acid from Acid Whey Permeate in a Membrane Recycle Bioreactor", *Enzyme Microb. Technol.*, 8:289–292 (May 1986).

Peters, E., "Microbiological and Biochemical Characterization of the Steeping Phase of the Corn Wet Milling Process" (abstract of a thesis submitted in partial fulfillment of requirements for degree), University of Iowa, pp. i–v, 39–57, 62–64, 77–79, 83–100, 105–107, 115 (May 1996).

Porro, D., et al., "Development of Metabolically Engineered *Saccharomyces cerevisiae* Cells for the Production of Lactic Acid", *Biotechnol. Prog.* 11:294–298 (1995).

Yabannavar, V., et al., "Extractive Fermentation for Lactic Acid Production", *Biotechnology and Bioengineering*, 37:1095–1100 (1991).

Yang, C., et al., "Lactic Acid Production by Pellet–Form *Rhizopus oryzae* in a Submerged System", *Applied Biochemistry and Biotechnology*, 51/52:57–71 (1995).

Ye, K., et al., "Performance Improvement of Lactic Acid Fermentation by Multistage Extractive Fermentation", *Journal of Fermentation and Bioengineering*, 81(3): 240–246 (1996).

Grimont, F., et al., "Ribosomal Ribonucleic Acid Gene Restriction Patterns as Potential Taxonomic Tools," *Ann. Inst. Pasteur/Microbiol.* (Paris), 1378:165–175, (1986).

Jacquet, et al., "Typing of Listeria monocytogenes by Restriction Polymorphism of the Ribosomal Ribonucleic Acid Gene Region," *Zbl. Bakt.*, 276:356–365, (1992).

Genga, A. M., et al., "Mitrochondrial NAD, L–Lactate Dehydrogenase And NAD, D–Lactate Dehydrogenase In The Yeast *Saccharomyces Cerevisiae*," *Microbiologica*, 1:1–8 (1983).

Peters, Jr., E. M. et al., "Microbiological And Biochemical Characterization Of The Steeping Phase Of The Corn Wet Milling Process," *An Abstract of a Thesis submitted to The University of Iowa*, 1–189 (May 1996).

Porro, D. et al., "Production of Lactic Acid From Engineered *Saccharomyces Cerevisiae* Cells," *Med. Fac. Landbouww. Univ. Gent*, 59(4b):2303–2311 (1994).

* cited by examiner

FIG. 2

| RIBO GROUP | STRAIN # |
|---|---|
| MIL 4-1132-S-1 | 127 |
| MIL 4-1132-S-2 | 132 |
| MIL 4-1132-S-3 | 140 |
| MIL 4-1132-S-7 | 90 |
| MIL 4-1135-S-4 | 114 |
| MIL 4-1135-S-4 | 119 |
| MIL 4-1132-S-8 | 79 |

LOW PH LACTIC ACID FERMENTATION

BACKGROUND OF THE INVENTION

Lactic acid and its salts have long been utilized in a wide variety of applications in the chemical, cosmetic, food and pharmaceutical industries. More recently, new bioengineering materials based on lactate, such as biodegradable lactide polymers, have kindled an increased demand for lactate and especially for the free acid form of either L- or D-lactate. The use of lactic acid in the production of various industrial polymers has been described, for example, in U.S. Pat. Nos. 5,142,023; 5,247,058; 5,258,488; 5,357,035; 5,338,822; 5,446,123; 5,539,081; 5,525,706; 5,475,080; 5,359,026; 5,484,881; 5,585,191; 5,536,807; 5,247,059; 5,274,073; 5,510,526; and 5,594,095. (The complete disclosures of these seventeen patents, which are owned by the assignee of the present application, Cargill, Inc. of Minneapolis, Minnesota, are incorporated herein by reference.)

While chemical processes can be used to produce lactic acid, the rising cost of petrochemical feedstocks and the need to resolve the racemic lactate mixture produced by conventional chemical methods, make fermentation methods an attractive alternative for the manufacture of lactate enriched in one of its optical isomers. The processes used to produce biodegradable lactide polymers typically require the free acid form of either L- or D-lactate as a starting material. Unfortunately, as with most organic acid fermentations, the end-product inhibition by the organic acid (lactic acid in this instance) can be a major obstacle to efficient fermentation. Bacterial strains typically employed in lactate fermentations may be inhibited by low pH in addition to lactate concentration. To overcome this problem, industrial lactate fermentation processes are typically run at a higher pH, e.g., at least about 5.0 and often at or above 6.0. This results in the production of a lactate product which is essentially all present in the form of a salt. Additional process step(s) are typically required to remove the cationic counterion and isolate the desired free lactic acid. Moreover, since high concentrations of certain salts, e.g., sodium cations, may have an inhibitory effect on fermentation, the type and/or amount of salt present can also influence the efficiency of the fermentation.

The production of racemic lactate from enzyme-thinned corn starch using lactobacillus amylovorus has been reported. While relatively high production levels at pH as low as 4.2 have been reported, this fermentation does not provide lactate enriched in either optical isomer.

A number of approaches for improving the efficiency of lactate fermentations have been reported. Several of these involve removal of free lactic acid from the fermentation broth on a continuous basis. For example, electrodialysis has been used to reduce the end product inhibition through removal of lactate from the fermentation broth. The high cost of dialysis membranes coupled with a low lactate gradient has generally lowered the attractiveness of this approach. Ion exchange and the use of polyvinylpyridine to remove lactate from the fermentation medium have also been reported. Yet another method which was described recently, involves a multistage extraction procedure. This process involves an extraction of lactate from the broth with a tertiary amine in an attempt to keep the broth pH from dropping to a value which inhibits further lactate production. The lactate production levels reportedly achieved via this method are still, however, quite low. Utilization of this method may also require that the extracted fermentation broth be subjected to a second extraction to at least reduce the residual concentration of tertiary amine extractant before recycling the extracted broth back into the fermentation reaction.

All of these approaches to producing lactic acid in its free acid form based on fermentation of lactobacillus suffer from one or more disadvantages. Alternative approaches based on the fermentations of other more acid tolerant microorganisms have also been reported. Yeasts, such as *Saccharomyces cerevisiae*, are capable of growth at much lower pH than lactobacillus. Recombinant yeast strains have been produced by introducing the lactate dehydrogenase gene from a bacterial (lactobactobacillus) or mammalian (bovine) source into *Saccharomyces cerevisiae*. The recombinant yeast strains are reportedly able to produce lactate at or below the $pK_a$ of lactic acid (about 3.8). Ethanol is, however, the major fermentation product generated by the these recombinant yeast strains. This both lowers the efficiency of lactate production and introduces additional potential issues with regard to the separation and purification of free lactic acid. Lactic acid production by a pellet form of the fungus, *Rhizopus orgyzae*, has also been reported. This fungal fermentation also typically produces glycerol and/or ethanol as major byproducts. The yield of free lactic acid was optimized in this instance by continuous removal from the fermentation broth using a polyvinylpyridine ("IPVP") column. No lactate concentrations higher than about 25 g/L were reported to have been generated using the Rhizopus/PVP method.

SUMMARY OF THE INVENTION

The present invention relates to the production of lactate via fermentation. It particularly concerns fermentation with acid-tolerant bacteria to produce a fermentation broth with high levels of free lactic acid. The presence of the high level of free lactic acid can facilitate the down stream processing required to isolate lactate in its free acid form from the broth.

The process provided herein for producing lactic acid includes incubating acid-tolerant bacteria, such as acid-tolerant homolactic lactobacillus, in nutrient medium at a pH which furnishes a substantial portion of the lactate product in the free acid form. Herein, when the term "acid-tolerant" is employed in reference to bacteria, the intent is to refer to bacteria which are capable of producing lactate at a pH sufficient to furnish a substantial portion of the lactate product in the free acid form. The acid-tolerant bacteria are typically capable of producing at least about 25 g/L free lactic acid. Such bacteria generally can also produce at least about 50 g/L lactate in nutrient medium at an "average incubation pH" of no more than about 4.2.

If fermentation is not carried out to a point where the limiting lactate concentration is reached, the "average incubation pH" is determined based on an average of the pH values measured at ten(10) or more equal time intervals over the course of the fermentation. The present fermentation process may be run in a continuous fashion. Under such conditions, steady state conditions (in terms of pH, lactate concentration and nutrient concentrations) are generally achieved and maintained after an initial startup phase has been concluded. When fermentation is conducted in this manner, the average incubation pH is the average pH of the broth after the initial startup phase has been completed, i.e., the pH during the startup phase is ignored in determining the average incubation pH.

If fermentation is carried out to a point where pH and/or lactic acid concentration inhibits further lactate production, the "average incubation pH" is determined based on an average of the pH values measured at ten(10) or more equal time intervals over the time period necessary to produce 90% of the limiting lactate concentration. As used herein, the "limiting lactate concentration" is the lactate concentration under a given set of incubation conditions (nutrient medium, temperature, degree of aeration) at which pH and/or lactic acid concentration generated by the fermentation inhibits further lactate production. As used herein, the term "limiting incubation pH" means the pH of the fermentation broth for a given set of incubation conditions at which the pH and/or lactic acid concentration inhibits further lactate production. Inhibition of lactate production is considered to have occurred when the amount of lactate produced does not increase by more than about 3% upon further incubation for a period of up to about twelve (12) hours under the same conditions. This definition presumes that sufficient nutrients for lactate production are still available in the fermentation broth.

Herein the terms "nutrient medium" and "fermentation broth" are used interchangeably. These terms refer to both (i) media in the form originally provided to the acid-tolerant bacteria as a source of nutrient and (ii) media produced after some or all of the originally provided nutrients have been consumed and fermentation products including lactate have been excreted into the media by the bacteria.

In the present process, the pH of the fermentation broth after incubation of the acid-tolerant bacteria to produce lactate is typically no more than about 4.2 ("final incubation pH"). As referred to herein, the "final incubation pH" is the pH of the fermentation broth at the point that growth and/or lactate production by the acid-tolerant bacteria ceases. The cessation of growth and/or lactate production may be the result of a change in reaction temperature, the exhaustion of one or more necessary nutrients in the fermentation broth, a deliberate change in pH, or the separation of the fermentation broth from the bacterial cells. In those instances where fermentation is arrested by the addition of sufficient acid or base to the broth to stop lactate production, the final incubation pH is defined to be the pH of the nutrient medium just prior to the addition. Alternatively, growth and/or lactate production may stop due to the accumulation of one or more fermentation products and/or a change in broth pH resulting from the accumulation of fermentation products, i.e., the fermentation reaction has reached a self limiting point for the given set of incubation conditions. As noted above, it is quite common for bacterial fermentations which produce an organic acid such as lactic acid to be subject to end-product inhibition.

The term "lactate" as used in this application refers to 2-hydroxypropionate in either its free acid or salt form. The terms "lactic acid" and "free lactic acid" are employed interchangeably herein to refer to the acid form, i.e., 2-hydroxypropionic acid. The salt form of lactate is specifically referred to herein as a lactate salt, e.g., as either the sodium salt of lactic acid or sodium lactate.

The present invention also provides acid-tolerant homolactic bacteria. The acid-tolerant homolactic bacteria are generally capable of producing at least about 25 g/L free lactic acid at an incubation temperature of at least about 40° C. Another embodiment of the present acid-tolerant bacteria is capable of producing at least about 50 g/L lactate at a temperature above about 40° C. and an average incubation pH of no more than about 4.2. Typically, the acid-tolerant bacteria is capable satisfying both of these measures of lactate productivity.

BRIEF DESCRIPTION OF THE DRAWINGS

FIG. 2 is a graph showing the ribotype patterns for a number of lactate-producing bacterial strains isolated from corn steep water.

DETAILED DESCRIPTION

Figure 1:
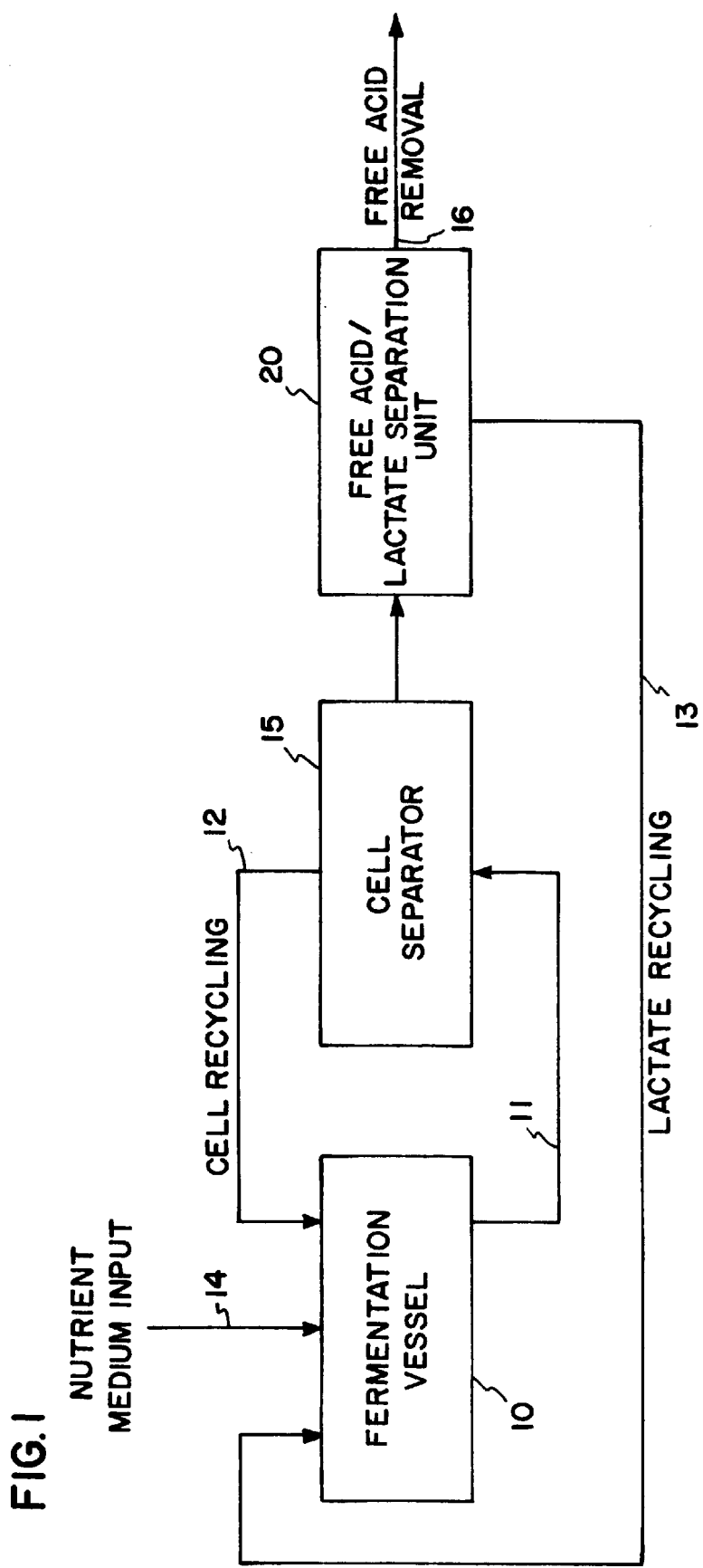
FIG. 1 is a schematic depiction of a flow diagram of an fermentation process which includes the coupled removal of free lactic acid.

The present process allows the efficient production of lactate and, in particular, the efficient production of high concentrations of free lactic acid via incubation of an acid-tolerant homolactic bacteria in a suitable nutrient medium. The acid-tolerant homolactic bacteria may be isolated from the corn steep water of a commercial corn milling facility. While different bacteria of this type may produce either racemic lactate, or lactate predominantly in either the D- or L-isomeric form, the present process preferably employs a homolactic bacteria which produces predominantly L- or D-lactate, and most preferably produces L-lactate in optically pure form.

The present process allows the efficient production of high concentrations of free acid form of an optical isomer of lactic acid. This efficiency may be expressed in a variety of manners. The concentration of free lactic acid in the fermentation broth serves as one measure of the overall productivity of the process. The present process typically generates a solution including at least about 25 g/L, preferably at least about 30 g/L, and more preferably at least about 40 g/L free lactic acid. Most preferably, the process produces these levels of either free L-lactic acid or free D-lactic acid. The optical purity of the lactate (and free lactic acid) produced is preferably at least about 50%, more preferably at least about 80% and, most preferably, one optical isomer of lactate is produced in essentially pure form.

As noted above, typically, the lactate produced by the present process is predominantly in the form of L-lactate. For example, one embodiment of the process includes incubating an acid-tolerant homolactic bacteria in nutrient medium to produce lactate which includes at least about 75 wt. % L-lactate (i.e., L-lactate having an optical purity of at least about 50%). Preferably, the optical purity of the lactate produced by the present process is at least about 80%, and more preferably at least about 90% (e.g., includes at least about 95 wt. % L-lactate). Most preferably, the present process produces L- or D-lactate in essentially optically pure form (i.e., the lactate produced contains 99 wt. % or higher of a single optical isomer).

The amount of free lactic acid present in a solution is a function of both the pH of the solution and the overall concentration of lactate in the mixture. Thus, specifying these two parameters for a given solution, such as a fermentation broth, effectively specifies the free lactic acid concentration. The present process is capable of generating a solution which includes at least about 50 g/L, preferably at least about 80 g/L, and more preferably at least about 100 g/L lactate at a relatively low pH. The lower the solution pH, the higher the percentage of the lactate which is present in its free acid form. For example, where the medium pH is equal to the $pK_a$ of lactic acid (about 3.8), 50% of the lactate is present in the free acid form. At pH 4.2, about 31% of the lactate as a free acid and at pH 4.0 and 3.9, about 41% and 47% respectively of the lactate is present in the free acid form. The fraction of free lactic acid is even lower at higher pH, 18% at pH 4.5 and 6.6% at pH 5.0.

The pH of the broth during the incubation step can be expressed in several different ways, e.g., in terms of the average incubation pH or the final incubation pH. The present fermentation process is typically capable of producing high levels of lactate at an average incubation pH of no more than about 4.3, preferably no more than about 4.2, and more preferably no more than about 4.0. Alternatively, the pH of the broth during incubation can be expressed in terms of the final incubation pH. The present process typically allows the production of high lactate concentrations at a final incubation pH of no more than about 4.2, preferably no more than about 4.0, and more preferably no more than about 3.9. Particularly effective embodiments of the present fermentation process are capable of producing at least about 80 g/L lactate at an average incubation pH of no more than about 4.0 and/or a final incubation pH of no more than about 3.9.

The present fermentation process may be run in a continuous fashion where a fraction of the fermentation broth is removed as the fermentation proceeds. This may be done either continuously or at periodic intervals. Sufficient nutrient medium is typically added to the reactor to maintain a constant liquid volume. Under such fermentation conditions, steady state conditions (in terms of pH, lactate concentration and nutrient concentrations) are generally achieved and maintained after an initial startup phase has been concluded. When fermentation is conducted in this manner, the average incubation pH (the pH during the startup phase is ignored) and the final incubation pH of the broth are essentially the same. Under such conditions, fermentation is typically carried out at a pH of no more than about 4.2, preferably no more than about 4.0, and more preferably no more than about 3.9.

Although the present incubation process may be carried out at relatively low temperatures, e.g., about 30° C. to about 38° C., the acid-tolerant homolactic bacteria is typically incubated in a suitable nutrient medium at a temperature of at least about 43° C., and more preferably at about 45° C. to about 52° C. Most preferably, the fermentation is carried out at about 47° C. to about 50° C. There are a number of advantages of operating the fermentation at these temperatures. The chances of complications due to growth of other competing organisms is lessened in this temperature range. In addition, at higher temperatures, the reaction generally proceeds at a faster rate allowing efficient utilization of process equipment. If fermentation is carried out at too high a temperature, typically at about 54° C. or above, growth and/or lactate production by the homolactic bacteria may be negligible. It may be possible, however, using standard selection techniques to identify mutant homolactic bacterial strains which are capable of growth and lactate production at temperatures of 55° C. and above.

As described herein "nutrient medium" refers to a water based composition including minerals and their salts necessary for growth of the bacterium of the present invention. The nutrient medium typically contains effective amounts of a carbon source, a nitrogen source, a phosphate source, a sulfate source, calcium and trace elements. The term "trace elements" refers to elements essential for growth in trace concentrations i.e., minute fractions of 1 percent (1000 ppm or less).

The bacteria of the present invention typically can utilize a number of carbon and energy sources for growth and/or lactate production, such as glucose, fructose, galactose, melibiose, sucrose, raffinose, and/or stachyose. Some of the bacteria may be able to use all or most of these sugars as a source of carbon and energy while other strains are more fastidious and may only be able to grow on one or two sugars from the list. In other instances, a starch (such corn starch) or a hydrolysate thereof may be used as primary carbohydrate source.

As used herein, "corn steep water" refers to water obtained from corn steeping tanks as well as other solutions derived therefrom having substantially the same spectrum of nutrients.

For example, corn steep liquor (also sometimes referred to as "heavy steep water") is a concentrated form of corn steep water obtained by removal of water and other volatile components, typically under vacuum. Corn steep liquor typically has a dry solids content of about 35 wt. % to about 50 wt. %. The corn steep liquor used in the experiments described in the Examples herein had a dry solids content of 36 wt. % and is referred to herein as "CSL." Corn steep waters obtained directly from corn steeping tanks and/or associated lines jsut before concentration to produce corn steep liquor generally have dry solids contents in the range of about 10 wt. % to about 15 wt. % and are referred to herein as "light steep water" ("LSW"). Light steep water typically has an $SO_2$ content of no more than about 500 ppm. The steep water used to supplement the nutrient medium used in the present process preferably has an $SO_2$ content of no more than about 300 ppm and, more preferably, no more than about 200 ppm. The light steep water used in the experiments described in the Examples herein had a dry solids content of 12 wt. %.

In situations where one or more homolactic strains isolated from corn steep water are to be used to produce lactate, the nutrient medium typically includes corn steep water corresponding to at least about 15 g/L steep water dry solids. Preferably, the nutrient medium includes corn steep water corresponding to at least about 25 g/L and, more preferably, at least about 30 g/L steep water dry solids.

One example of a suitable nutrient medium for use the present fermentation process is MRS medium (such as the MRS medium commercially available from Becton Dickinson & Co.) or the like. The MRS medium is generally supplemented with corn steep water to provide a nitrogen source and general source of nutrients as well as with additional carbohydrate (such as glucose or fructose) as a carbon and energy source. Typical media suitable for use in the present process also include magnesium salt(s), manganese salt(s), phosphate salt(s), potassium salt(s) and/or citrate salt(s). It may, howver, not be necessary to add specific amounts of such salts to the medium. Often, the nutrient medium also includes a nonionic surfactant, such as fatty acid monoester of a polyoxyethylene derivative of sorbitan (e.g., Tween® 80 which is polyoxyethylene (20) sorbitan monooleate).

The medium may be prepared by using separate salts as sources of each of the various inorganic components. Alternatively, a single salt which acts as a source of more than one component may be used to prepare the nutrient medium. For example, potassium hydrogen phosphate ($K_2HPO_4$) may be added as a source of both potassium cations and phosphate anions. It will be recognized that after the various components have been dissolved in water during the preparation of the nutrient medium, an interchange of cations and anions among the various dissolved salts present will occur. For example, if magnesium sulfate and ammonium citrate are added to water during the preparation of the medium, the resulting solution will also include some ammonium sulfate and magnesium citrate species in addition to magnesium sulfate and ammonium citrate species. One type of nutrient medium which is particularly suitable for use in the present fermentation process includes corn steep water supplemented with glucose and/or fructose as an additional carbon and energy source.

One example of a suitable medium for use in the present invention includes:

corn steep water corresponding to about 30 to about 45 g/L steep water dry solids;

about 80 to about 120 g/L glucose, fructose or a mixture thereof;

about 0 to about 10 g/L yeast extract;

about 0 to about 1 g/L of a nonionic surfactant such as Tween® 80;

about 0 to about 2 g/L potassium hydrogen phosphate ($K_2HPO_4$)

about 0 to about 0.2 g/L magnesium sulfate ($MgSO_4$);

about 0 to about 0.05 g/L manganese sulfate ($MnSO_4$);

about 0 to about 2 g/L ammonium citrate; and optionally, about 10 to about 50 g/L calcium carbonate ($CaCO_3$).

For the reasons discussed above, the amounts refer to the quantities of the various materials added to form the medium and not to the actual concentrations of these species in the nutrient medium. In making up such a nutrient medium, all of the components except the nonionic surfactant and the calcium carbonate are generally dissolved in an appropriate amount of water and autoclave sterilized. The nonionic surfactant is typically added to the autoclaved medium while it is still at a temperature of close to about 100° C. The resulting solution is then typically allowed to cool to about 60° C. or lower before the calcium carbonate is added.

It has been found that suitable nutrient mediums for use in the present process preferably include at least about 50 g/L of carbohydrate. More preferably, the nutrient medium include at least about 70 g/L and, most preferably, at least about 90 g/L of the carbohydrate. The carbohydrate typically is made up of glucose, fructose, galactose, melibiose, sucrose, raffinose, stachyose, or a mixture thereof. Glucose, fructose, and sucrose are particularly suitable for use as a carbon and energy source in the nutrient medium. It is generally not useful to incorporate more than about 150 g/L carbohydrate in the medium.

It has been found that it may be advantageous to include a base such as calcium carbonate ($CaCO_3$), sodium hydroxide (NaOH), ammonium hydroxide ($NH_4OH$) and/or sodium bicarbonate ($NaHCO_3$). Typically at least about 30 g/L calcium carbonate (or an equivalent amount of another base) is added to the nutrient medium. In some embodiments of the process, e.g., embodiments which produce higher levels of lactate, it may be preferred to include up to about 40 g/L calcium carbonate in the nutrient medium. While higher levels of base may be employed, due to limitations on the solubility of calcium carbonate salts and the desire to maintain a relatively low broth pH, it is generally not useful to incorporate more than about 100 g/L calcium carbonate in the medium. Very often, the entire amount of calcium carbonate present will not initially dissolve in the nutrient medium. As the fermentation proceeds, some of the calcium carbonate may react with the lactic acid being formed to generate calcium lactate. As this occurs, additional portions of the undissolved calcium carbonate may be drawn into solution. The overall effect is to neutralize a portion of the forming lactic acid and prevent the pH of the broth from dropping below a desired level (e.g., below about 3.8–3.9).

It may not be necessary to add a base such as calcium carbonate to achieve this effect. A solution containing a lactate salt (e.g., calcium, sodium or ammonium lactate) may be added to aid in buffering the pH of the fermentation broth. One example of a process in which this might occur would involve the separation of a fraction of the fermentation broth from the incubating bacteria, and recycling the portion back into the fermentation after removal of some or all of the free lactic acid in the fraction. Alternatively, calcium lactate might be isolated from the fermentation broth (e.g., in solid form), and mixed together with nutrient medium being added to the fermentation. Generally, addition of lactate salt as a buffering salt can be advantageous because it minimizes the amount of neutralizing base added to the fermentation broth thereby minimizing the amount of lactate produced that is converted to salt form.

Nutrient media including at least about 70 g/L glucose and/or fructose and at least about 20 g/L calcium carbonate are particularly suitable for use in the present process. Depending on the bacterial strain employed in the process, incorporation of corn steep water (e.g., in an amount equivalent to at least about 25 g/L corn steep water dry solids) in this nutrient medium may also be preferred. It is particularly useful to add corn steep water containing only the same chiral form of lactate to be generated by the fermentation process.

The strain of homolactic bacteria and the fermentation conditions are typically chosen such that free lactic acid is produced at a overall rate of at least about 0.5 g/L/hr, preferably at least about 1.0 g/L/hr, more preferably at least about 2.0 g/L/hr, and most preferably at least about 4.0 g/L/hr. As used herein, overall rate of production of either lactate or free lactic acid (or lactate) is calculated by dividing the total amount of free lactic acid (lactate) produced by the incubation time. For fermentations where a limiting lactate concentration is produced, the overall production rate of free lactic acid (lactate) is calculated over the time required to produce 90% of the limiting of free lactic acid (lactate) concentration.

The productivity of the present process may also be expressed in terms of the overall production rate for lactate. The present fermentation process is generally carried out under conditions which produce lactate at a overall rate of at least about 1.0 g/L/hr, preferably at least about 2.0 g/L/hr and, more preferably, at least about 3.0 g/L/hr. As indicated herein, lactate is preferably produced at these rates in a broth at an average incubation pH of no more than about 4.1, and more preferably, no more than about 4.0.

Suitable examples of homolactic bacteria for use in the present fermentation method may be readily isolated from samples of corn steep water, such as are found in commercial corn milling facilities. In addition, certain other homolactic bacteria isolated from different sources may also have the necessary capabilities to permit efficient low pH production of high levels of free lactic acid.

Since the homolactic bacteria found in corn steep water typically require a nutrient medium which includes corn steep water for growth, the initial step in a process for identifying and isolating such bacteria typically involves plating samples in a steep water-containing medium, such as 10 vol. % CSL-MRS agar, and then incubating the inoculated medium anaerobically at about 45–50° C. Bacterial isolates can easily be probed for heterolactic production by passing the isolate into a biphasic medium which only contains steep water in the lower phase. The growing strains are then monitored for the generation of gas at the bottom of the biphasic tubes. The isolated strains may be conveniently stored at low temperature (e.g., 4° C. or below) or maintained as a bench stock in a steep water/tomato juice/MRS agar growth medium. When desired, one or more acid-tolerant strains isolated in this fashion from corn steep water may be used as an inoculant in a lactic acid fermentation.

Using this type of methodology, steep water samples obtained from five different corn milling facilities in the United States as well as three corn milling facilities located in Turkey, England and the Netherlands were examined for lactate producing microorganisms. The isolated microorganisms were initially characterized as heterolactic (i.e., able to produce other fermentation products in addition to lactate) or homolactic producers. The homolactic strains were further characterized, inter alia, based on overall lactate production, optical activity of lactate produced and, in many instances, final incubation pH in the absence of base ($CaCO_3$) added to the fermentation medium. A total of 155 bacterial strains were isolated. Of the 109 strains which were characterized, 98 strains (90%) produced lactate as the sole fermentation product ("homolactic" strains). The remaining 11 strains (11%) produced other fermentation products in addition to lactate ("heterolactic" strains). Of the 98 homolactic strains, 22 were L-lactate producers, 18 were D-lactate producers, and 58 produced racemic lactate.

The present homolactic bacteria are generally capable of producing at least about 25 g/L free lactic acid. Most preferably, the bacteria are homolactic bacteria capable of producing at least about 30 g/L free L-lactic acid. In another embodiment of the invention, the homolactic bacteria is capable of generating a solution containing at least about 40 g/L, preferably at least about 75 g/L lactate, and preferably at least about 90 g/L lactate at an average incubation pH of no more than about 4.3. As discussed elsewhere herein, particularly effective strains of the present homolactic bacteria are capable of producing these levels of L-lactate (or D-lactate) at an average incubation pH of no more than about 4.0 and/or a final incubation pH of no more than about 3.9.

The present acid-tolerant homolactic bacteria is typically capable of growth and lactic acid production at temperatures between about 35° C. and about 53° C. Optimum temperature for growth generally ranges from about 43° C. to about 52° C. and, preferably, about 47° C. to about 50° C., although it has been demonstrated that the homolactic bacteria can grow at temperatures at or close to room temperature. Negligible lactate production by the bacteria typically occurs when the temperature is above about 53° C. or below about 30° C. The fermentation process is preferably conducted at about 47° C. to about 52° C., since yeasts and heterolactic lactobacilli are less thermotolerant and generally will not grow well, if at all, at these temperatures. Thus, in addition to enhancing lactate production, fermentation of the acid-tolerant homolactic bacteria at high temperature can decrease the possibility of problems associated with contamination by other organisms.

The present homolactic bacteria is typically capable of growth and lactate production at least within a pH range of about 3.7 to about 6.5 and preferably at least across a pH range from about 3.8 to about 5.0. Even though the bacteria may be able to produce lactate at a pH close to neutral (e.g., 6.0–6.5), bacteria employed in the present process preferably are capable of high levels of lactate at a pH where a substantial portion of the lactate exists is its free acid form. Preferred forms of the acid-tolerant homolactic bacteria are capable of significant lactate production (e.g., at least about 50 g/L) at a pH of 4.2 or below.

A variety of reactor configurations including packed bed reactors, continous stirred tank reactors, rotating biological contact reactors, sequencing batch reactors and fluidized bed reactors may be employed in the present process. The entire reaction may be performed in a single vessel having appropriate means to control the temperature of the fermentation broth or, alternatively fermentation may be carried out in a first vessel, the broth may be maintained at the desired temperature by passage through a heat exchanger, for example, a plate heat exchanger and recycled to the fermentation reaction. The latter arrangement can provide more rapid cooling of the reaction mixture and can in some instances be carried out at the same time that broth is passed through a membrane separation module to remove a portion of the broth (e.g., where the heat exchanger and membrane module are connected in series).

One commonly used configuration includes a membrane recycle bioreactor. Reactors of this type typically includes two modules, a fermentation vessel 10 and a membrane module 15 (see e.g., FIG. 1). These two modules may be connected by a pipe or be parts of a single apparatus.

In one embodiment of the invention, acid-tolerant homolactic bacteria may be incubated in a first portion of nutrient medium in the fermentation vessel to generate a first product solution including at least about 25 g/L free L-lactic acid. The resulting fermentation broth may be separated to provide a first fraction which includes free lactic acid and is substantially free of bacterial cells. This may be carried out by pumping a portion of the fermentation through a cell separator (e.g., a hollow fiber cell separator). The cell-containing fraction is typically recyled back into the fermentation vessel (see e.g., FIG. 1), while the lactic acid-containing fraction is split off for further processing. Additional nutrient medium is typically added to maintain the liquid volume in the fermentation vessel at a constant level. When fermentation is conducted in this manner, steady state conditions (in terms of pH, lactate concentration and nutrient concentrations) are generally achieved and maintained after an initial startup phase has been concluded.

When run in such a mode, the present fermentation is typically conducted such that the pH of the broth is maintained at about 4.2 or below and, preferably, in the range between about 3.7 and 4.0.

The lactic acid-containing fraction which is split off may be processed using a number of known methods to separate free lactic acid from the other components of the solution. For example, the lactic acid may be extracted from the solution using a tertiary amine-containing extractant. One example of a suitable extractant is a solution of Alamine 336 in octyl alcohol. Other methods which may be used to isolate the lactic acid include contacting the solution with a soild adsorbent, such as an ion exchange resin (e.g., a polyvinylpyridine column), distilling off a lactic acid containing fraction, or removal via membrane separation. Any of these type of separation methods may be used to process the lactic acid-containing fraction to generate a lactic acid-depleted fraction and a lactate isolate fraction. The lactic acid-depleted fraction may contain some lactate in the form of a lactate salt, such as calcium lactate. The lactate isolate fraction may be further processed using any of a variety of known methods to produce a purer form of free lactic acid.

The lactic acid-containing fraction may also be processed to separate out lactate salt (e.g., calcium lactate) in solid or solution form, leaving a solution enriched in free lactic acid. The lactate salt may be separated using a suitable technique such as extraction, crystallization, membrane separation and adsorbtion on a solid material (e.g., anion exchange resin). The lactate salt may be returned to the fermentation vessel where it can serve to buffer the pH of the solution and prevent the pH of the broth from dropping below a desired level. For example, by recycling a sufficient amount of calcium lactate as a buffering agent, the pH of the fermentation broth may be maintained at a value close to the $pK_a$ of lactic acid. Based on theory, the lactate salt will buffer production of an equivalent amount of new lactic acid production at a pH of 3.85. At pH 4.0, each equivalent of lactate salt will buffer production of 0.7 equivalent amount of new lactic acid production.

A variety of methods are available for processing lactate/lactic acid solutions involving generation of large amounts of lactic acid; for example, in solution at pHs no greater than about 4.8 (preferably no greater than about 4.2 or 4.3) from the fermentation broth; and, with a concomitant isolation (and if desired recycling) of lactate salt (typically calcium lactate, potassium lactate, sodium lactate and/or ammonium lactate). Such processes are described, for example, in commonly assigned (to Cargill, Inc. of Minnetonka, Minn.), co-filed, U.S. patent application entitled LACTIC ACID PROCESSING; METHODS; ARRANGEMENTS; AND, PRODUCTS, identifying Aharon M. Eyal, John N. Starr, Riki Canari, Betty Hazan, Rod Fisher, Jeffrey J. Kolstad, David R. Witzke, and Patrick R. Gruber as inventors (hereinafter referred to as the Starr et al application). The Starr et al application was filed on the same date of the present application (Oct. 14, 1997) and is incorporated herein by reference. Advantageous overall processes will depend, in part, upon selection, among the approaches, of the one which most readily facilitates an overall cost-effective and efficient processing scheme in large scale implementation.

The principle concerns in selecting overall processes relate to design of the system to accommodate the two objectives of:

1. Isolation of lactic acid products for follow-up processing, for example to generate polymer; and
2. Isolation of lactate salt, preferably in a form desirable for recycling to the fermentation broth.

Three general approaches concern:

1. Separation of the lactic acid from the solution leaving the lactate salt behind; and, if desired, direction of the residual solution having the lactate salt therein, after the separation, into a fermentor;
2. Isolation of the lactate salt from the solution; direction of the lactate salt, if desired, into a fermentor; and, a follow-up isolation of the lactic acid product from the residual solution after lactate salt separation; and,
3. Simultaneous separation of lactic acid into one stream and lactate salt into another, leaving residual mixture.

The techniques described in Starr et al. to achieve one or both of these objectives can be practiced on a variety of solutions of lactate material (i.e. solutions of lactic acid and dissolved lactate salt). These solutions may comprise fermentation broth or broth which has been removed from a fermentor and modified in some manner, for example by filtration or pH adjustment. Indeed the techniques can be applied to the solutions which are made in other manners as well. The techniques and proposals described therein, however, are particularly developed with a focus on efficient processing of fermentation broth solutions, especially relatively acidic ones, in which pH modification by addition of acid is not required and preferably has not occurred. Typical compositions in which these techniques can be applied, with respect to pH, would be at least 0.86 and less than 6.0. That is, typical compositions on which the techniques will be practiced, will have a pH within this range. For such compositions the molar ratio of free lactic acid to dissociated acid or dissolved lactate salt at 25° C., is within a range of about 1,000:1 to 0.007:1. More preferred processing will involve solutions with a pH in the order of about 1.98–5.00 (HLA:LA ratio within the range of about 75:1 to 0.070:1); and, most preferred processing will involve solutions having a pH within the range of about 3.0–4.5 (HLA:LA ratio within the range of about 7.0:1 to 0.23:1).

As indicated above, solutions within the most preferred pH range described above are readily obtained via the present fermentation process with substantial concentrations of the lactate material therein. Alternatively, other fermentation broths can be used, for example with pH adjustment by addition of acid typically to the most preferred pH range given.

Herein, there will sometimes be reference to "preferential separating" of: lactic acid from a composition containing lactic acid and lactate salt; or, lactate salt from composition containing lactic acid and lactate salt. The term "preferential separating" and variants thereof, in this context, is meant to refer to separation technique which preferentially removes one of the two components (lactic acid or lactate salt) with respect to the other. In typical preferred processing according to the present invention a mixture of lactic acid and lactate salt is divided into two "product streams". In one product stream, (i.e., the free lactic acid rich stream), preferably the molar ratio of free lactic acid to lactate salt obtained is at least 2/1 and preferably at least 3/1. With certain of the techniques described herein, ratios of at least 5/1 and indeed in ratios of 10/1 or more are readily obtainable.

The other product stream is the lactate salt rich stream. In this stream, preferably the molar ratio of free lactic acid to lactate salt is no greater than 0.5. With typical preferred processing as described herein ratios of no greater than 0.3, preferably no greater than 0.2 and most preferably 0.1 or lower are readily obtained.

Herein the term "stream" when used in the context indicated by the previous two paragraphs, is meant to refer to an isolated phase or product segment, without regard to whether that phase or product segment is a solution, solid or a mixture of materials. Thus, a "lactate acid rich stream" is merely a phase or mixture rich in lactic acid (versus lactate salt) by comparison to the original mixture processed; and, a "lactate salt rich stream" is a stream rich in lactate salt (versus lactic acid) by comparison to the original mixture processed.

When the product stream enriched in free lactic acid is obtained as a result of separating the free lactic acid from the mixture, for example from a fermentation broth, the remaining aqueous mixture after the free lactic acid removal will sometimes be referred to as "depleted" with respect to free lactic acid. Similarly, when the lactate salt enriched stream results from separation of the lactate salt from a mixture containing the free lactic acid and the lactate salt, the remaining mixture will sometimes be referred to as "depleted" with respect to the lactate salt.

Preferably, when the solution processed is a fermentation broth, the product stream enriched in lactate salt is provided and formed such that the weight ratio of impurities from the fermentor, to lactate salt therein, is lower than found in the fermentation broth, preferably by a factor of at least 5. This can be managed by techniques described herein concerning control over the particular approach selected for isolation of the lactate salt, as well as through use as various purification techniques, such as back washing or recrystallization.

Preferably, the lactate product stream is eventually isolated as an aqueous solution or mixture of an aqueous phase and a solid phase, for convenient recycling into a fermentation system, in order to maintain water balance. If concentration of an aqueous solution is used in order to facilitate the water balance in the broth, preferably relatively low-cost concentration techniques such as reverse osmosis and vapor recompression are used.

The invention will be further described by reference to the following examples. These examples illustrate but do not limit the scope of the invention that has been set forth herein. Variation within the concepts of the invention will be apparent.

EXAMPLE 1

Standard Fermentation Conditions

Unless otherwise indicated, the fermentation reactions describe in the following examples were run using a variety of growth media according to the following standard protocol.

Cells (250 ul) were passed from a bench stock of the particular strain in 40% tomato juice/40% LSW-MRS agar bottom phase/MRS top phase biphasic (TJ-SW-MRS biphasic) into fresh TJ-SW-MRS top phase biphasic medium and incubated under static conditions for 18–24hours at 47° C.

| MRS Medium (pH = 6.2) | |
|---|---|
| 10 g/L | pancreatic digest of gelatin |
| 8 g/L | beef extract |
| 4 g/L | yeast extract |
| 20 g/L | glucose |
| 2 g/L | $K_2HPO_4$ |
| 1 g/L | Tween[R] 80 |
| 5 g/L | sodium acetate |
| 5 g/L | ammonium citrate |
| 0.2 g/L | $MgSO_4$ |
| 0.05 g/L | $MnSO_4$ |

A 1.0 ml aliquot of the incubate in the fresh TJ-SW-MRS biphasic medium was used to inoculate 80 ml of Medium B supplemented with 10% CSL, glucose (60 g/L total concentration) and calsium carbonate (20 g/L) in a sealed serum bottle and incubated with agitation 18 hours at 47° C. in an environmental shaker.

| Medium B (pH = 4.7) | |
|---|---|
| 8–12 vol. % | corn steep liquor |
| 5 g/L | yeast extract |
| 50–100 g/L | glucose |
| 2 g/L | $K_2HPO_4$ |
| 1 g/L | Tween[R] 80 |
| 2 g/L | ammonium citrate |
| 0.2 g/L | $MgSO_4$ |

| -continued | |
|---|---|
| Medium B (pH = 4.7) | |
| 0.05 g/L | $MnSO_4$ |
| 20–40 g/L | $CaCO_3$ |

Fermenters containing Medium B with the desired levels of glucose and calcium carbonate (e.g., 90 g/L glucose and 33.4 g/L calcium carbonate) were inoculated with 10% (v/v) of the 18 hours old culture. Fermentation was run at 47–49° C. with stirring at 150 rpm and fermentation jars 70–80% full. Running the fermentation jars at this liquid volume level ensured that the medium did not become highly aerobic.

EXAMPLE 2

Isolation of Acid-Tolerant Homolactic Strains Without pH Control

Homolactatic bacterial strains were isolated from samples of corn steep water obtained from eight different industrial corn milling facilities. The facilities were located in Blair, Nebraska; Edyville, Iowa; Cedar Rapids, Iowa; Dayton, Ohio; Memphis, Tennessee; Istanbul, Turkey; Tillbury, England; and Bergen Op Zoon, the Netherlands.

The strains were isolated by obtaining samples of steep water from commercial corn milling facilities. The samples were plated on 10% CSL-MRS agar plates (pH 5.0) and incubated anaerobically at 47° C. Colonies were restreaked for isolation on 10% CSL-MRS agar plates. Isolates were then passed into a 40% LSW-40 tomato juice-MRS bottom phase/MRS top phase biphasic medium (pH 6.0) for maintenance purposes. The isolated strains were screened for heterolactic production by monitoring for the formation of gas ($CO_2$) in the bottom of the tube. The homolactic isolates were then screened in MRS Medium supplemented with 10 vol. % CSL and 30 g/L glucose for lactate yield and the optical purity of the lactate produced. The results are shown in Table 1 below.

The isolated bacterial strains were identified as either homolactate producers ("homolactate") or heterolactate producers ("heterolactic"). Based on fermentation in MRS medium supplemented with 10 vol. % corn steep liquor ("CSL"), the isolated homolactic bacterial strains were characterized in terms of overall lactate production, final fermentation pH and % L-lactate produced (see Table 1 below). Since about 50% of the lactate in the added corn steep liquor ("CSL") was typically D-lactate, strains which produced at least about 70% L-lactate were considered to be L-lactate producing strains. This assumption was confirmed by subsequent experiments under conditions where D-lactate contamination levels in the product arising from steep water present in the nutrient medium were lower (e.g., higher lactate production levels or using corn steep water having greater than 80% L-lactate (as a fraction of the total lactate)).

The fermentations were carried out at 48° C. under the standard conditions described in Example 1. The results are shown in Table 1 below.

EXAMPLE 3

Isolation of Acid-Tolerant Homolactic Strains Using Added Base

An additional set of homolactic strains were isolated from corn steep water samples obtained from the corn milling facilities in Edyville (IA), Cedar Rapids (IA), and Blair (Nebr.). The isolation procedure employed was the same as described in Example 2. The isolated homolactic strains were characterized based on fermentations carried out in Medium B supplemented with 10 vol. % CSL, 90 g/L glucose and 33 g/L $CaCO_3$. The overall lactate production and/or percentage L-lactate produced were measured for this set of strains. The results are shown in Table 2 below.

TABLE 2

Isolated Homolactic Strains

| Strain No. | g/L Lactate | % L-Lac. |
|---|---|---|
| 90 | 62 | 81 |
| 92 | 67.9 | 59 |
| 95 | 62.47 | 44 |
| 99 | 63.17 | 78 |
| 103 | 58.53 | 75 |
| 104 | 65.18 | 75 |
| 109 | 66.26 | 83 |
| 114 | 58.6 | 46 |
| 117 | 47.99 | 62 |
| 127 | 49.54 | 44 |
| 129 | 68.75 | 77 |
| 132 | 59.12 | 95 |
| 133 | 60.37 | 95 |
| 134 | 28.87 | 63 |
| 136 | 54.1 | 41 |
| 139 | 66.08 | 47 |
| 140 | 57.18 | 94 |

EXAMPLE 4

Effect of Added Base on Lactate Production of Added Base on Lactate Production

A number of the strains descrived in Example 2 which had been identified as L-lactate producers were screened to examine the effect of added base ($CaCO_3$) on lactate production. The fermentations were carried out at 48° C. in MRS medium supplemented with 10% CSL and 30 g/L glucose. For the determinations made in the presence of added base, MRS medium supplemented with 10% CSL, 30 g/L glucose 20 g/L $CaCO_3$ were used.

TABLE 3

Effect of $CaCO_3$ on Lactate Production

| | Lactate Production (g/L) | |
|---|---|---|
| Strain # | No Base | 20 g/L $CaCO_3$ |
| 6 | 21 | 42 |
| 10 | 20 | 32 |
| 14 | 23 | 37 |
| 19 | 17 | 33 |
| 21 | 26 | 49 |
| 22 | 19 | 34 |
| 23 | 28 | 47 |
| 24 | 18 | 46 |
| 41 | 24 | 48 |
| 42 | 27 | 49 |
| 43 | 23 | 42 |
| 44 | 24 | 39 |
| 45 | 21 | 37 |
| 46 | 21 | 47 |
| 47 | 21 | 37 |
| 51 | 24 | 37 |

EXAMPLE 5

L-Lactate Production

The level of L-lactate production was characterized for a number of the strains described in Example 2. The fermentations were carried out at 48° C. in MRS medium supplemented with 10% CSL, 30 g/L glucose and 20 g/L $CaCO_3$.

TABLE 4

L-Lactate Production

| Strain # | % L-Lactate | Lactate Produced (g/L) |
|---|---|---|
| 10 | 87% | 39.12 |
| 14 | 79% | 21.11 |
| 21 | 85% | 38.56 |
| 23 | 85% | 35.69 |
| 24 | 84% | 31.78 |
| 41 | 86% | 38.10 |
| 42 | 83% | 30.62 |
| 43 | 80% | 25.17 |
| 44 | 84% | 31.75 |
| 46 | 86% | 36.12 |

EXAMPLE 6

Lactate Production by ATCC Deposited Lactobacillus Strains

The lactate productivity of a number of known lactobacillus strains isolated from sources other than corn steep water was examined. Samples of eleven different strains were obtained from the American Tissue Culture Collection (Rockville, Md.) and screened for total lactate production and final incubation pH based on fermentation at 37° C. in MRS medium supplemented with 75 g/L glucose and 30 g/L calcium carbonate. The results are shown below in Table 5. All of the strains exhibited poor growth at 47° C. and were inhibited by the presence of corn steep water in the nutrient medium. While the nutrient requirements of the ATCC deposited strains are different from the strains isolated from corn steep water, several of the ATCC deposited strains appear to be capable of producing relatively high concentrations of free lactic acid. In particular *Lactobacillus helviticus* (ATCC #15009; 66 g/L lactate at a final incubation pH of 4.03), *Lactobacillus paracasei* tolerans (ATCC #25599; 66 g/L lactate at a final incubation pH of 4.04), and *Lactobacillus salivarius salivarius* (ATCC #11741; 64 g/L lactate at a final incubation pH of 4.12) appear to offer potential as high productivity free lactic acid producers. The optical purity of the lactate produced by a number of the strains was determined. None of the strains capable of producing a relatively high concentration of free lactic acid was an L-lactate producing strain.

TABLE 5

Lactate Production by ATCC Lactobacillus Strains

| ATCC # | Lactobacillus | Lac | % L-Lac | pH |
|---|---|---|---|---|
| 12315 | L. deibrueckii lactic | 47 | 42 | 4.93 |
| 11741 | L. salivarius salivarius | 64 | 52 | 4.12 |
| 25302 | L. paracasei paracasei | 52 | 69 | 4.76 |
| 25258 | L. jensenii | 3 | — | 6.25 |
| 15009 | L. helveticus | 66 | 53 | 4.03 |
| 33409 | L. delbrueckii bulgaricus | 18 | 54 | 5.45 |
| 25599 | L. paracasei tolerans | 66 | 53 | 4.04 |
| 39392 | L. casei casei | 50 | 12 | 4.71 |
| 33323 | L. grasseri | 18 | — | 5.62 |
| 4536 | L. acidophilus | 40 | — | 5.43 |
| 35046 | L. animalis | 51 | — | 4.78 |

EXAMPLE 7

$SO_2$ Tolerance of Homolactic Strain #41

The effect of varying levels of sulfur dioxide ($SO_2$) on the lactate productivity of the homolactic strain #41 was examined. The effects of varying sulfur dioxide concentration on lactate production were examined using strain #41. The fermentations were carried out in MRS Medium supplemented with 10 vol. % CSL, 30 g/L glucose and 20 g/L $CaCO_3$ via the standard fermentation protocol described in Example 1. The results shown in Table 6 below demonstrate that the strain #41 is capable of producing lactate in the presence of $SO_2$ concentrations of up to at least about 600 ppm. In similar fermentation carried out in the presence of 800 ppm, strain #41 started producing lactate after a dormant phase of 144 hours.

TABLE 6

$SO_2$ Tolerance of Homolactic Strain #41

| | Lactate Production (g/L) | | |
|---|---|---|---|
| $SO_2$ Conc. | 24 hr. | 48 hr. | 72 hr. |
| 200 ppm | 11 | 48 | 66 |
| 400 ppm | 9 | 27 | 55 |
| 600 ppm | 9 | 11 | 43 |

EXAMPLE 8

Effect of Temperature on Lactate Production

The lactate productivity of the homolactic strain #41 was determined over a range of temperatures between 41° C. and 54° C. The fermentations were carried out in Medium B supplemented with 10 vol. % CSL, 60 g/L glucose and 20 g/L calcium carbonate. The results shown in Table 7 below establish that the optimum temperature range for lactate production by the strain #41 is from 44° C. to 54° C.

TABLE 7

Temperature Dependence of Lactate Production

| | Lactate Production (g/L) | | |
|---|---|---|---|
| Temp. (° C.) | 24 hr. | 48 hr. | 72 hr. |
| 41° C. | 14 | 51 | 68 |
| 44° C. | 25 | 55 | 68 |
| 47° C. | 26 | 50 | 63 |
| 50° C. | 31 | 52 | 57 |
| 54° C. | 9 | 19 | 23 |

EXAMPLE 9

Effect of Steep Water Concentration on Lactate Production

Fermentations employing a number of the L-lactate producing strains described in Example 2 were conducted to examine the effect of varying amounts of corn steep liquor in the growth medium on lactate production. The fermentations were conducted at 48° C. in Medium A (see below) supplemented with 50 g/L glucose, 20 g/L $CaCO_3$, and either 1%, 5% or 10% CSL.

| Medium A (pH = 5.0) | |
|---|---|
| 10 g/L | yeast extract |
| 0.2% | $K_2HPO_4$ |
| 1 g/L | Tween$^R$ 80 |
| 0.2% | ammonium citrate |
| 0.005% | $MnSO_4$ $4H_2O$ |
| 0.02% | $MgSO_4$ $7H_2O$ |
| | Added carbon/energy source |
| | Added nitrogen source |
| | $CaCO_3$ added to modulate pH |

TABLE 8

Effect of Steep Water on Lactate Production

| | Lactate Production (g/L) | | |
|---|---|---|---|
| Strain # | 1% CSL | 5% CSL | 10% CSL |
| 10 | 1 | 19 | 31 |
| 23 | 1 | 10 | 32 |
| 24 | 1 | 6 | 22 |
| 41 | 1 | 9 | 33 |
| 45 | 1 | 8 | 35 |

EXAMPLE 10

Characterization of Homolactic Strains Baaed on Ribotype

A number of the L-lactate producing homolactic bacterial strains isolated from corn steep water were categorized based on riboprint pattern analysis (see, e.g., Jaquet et al., Zbl. Bakt., 276, 356–365 (1992)). This technique is based on digestion of DNA from a single colony of the strain in question using an EciRI restriction enzyme and hybridization after size separation on an agarose gel with a chemically labeled rRNA operon from E. coli. The resulting pattern is a direct indicator of genetic relationships between organisms and has been used to provide identification between four genera of bacteria (Samonella, Listeria, Staphylococcus and E. coli) as well as for the taxonomical identification of closely related gram positive and gram negative strains.

The results of ribotyping of seven of the lactate producing strains isolated from corn steep water are shown in FIG. 2. Strains given the same RiboGroup designation are likely to be identified to the same taxon level as identical. The ribotypes exhibited by the seven strains shown in FIG. 2 did not match the patterns of any of 30 different lactic acid bacterial strains in a commercial laboratory's computer database. Among the strains in the database which did not provide a match were Lactobacillus acidophilus, Lactobacillus animalis, Lactobacillus delbrueckii, Lactobacillus helveticus, Lactobacillus amylovorus and Lactobacillus salivarius. The ribotypes of the strains listed in FIG. 2 also did not provide a match with the patterns from Lactobacillus agilis, Lactobacillus brevis, Lactobacillus buchneri, Lactobacillus confusus, Lactobacillus coryniformis, Lactobacillus curvatus, Lactobacillus farciminis, Lactobacillus kefir, Lactobacillus murinus, Lactobacillus pentosus, Lactobacillus plan tarum, Lactobacillus sake, and Lactobacillus suebicus. The ribotype patterns shown in FIG. 2 also did not provide a match with Lactococcus garviae, Lactococcus lactis, and Lactococcus raffinolactis or with Leuconostoc carnosum, Leuconostoc citreum, Leuconostoc mesenteroides, Leuconostoc paramesenteroides, Pediococcus acidilactici, Pediococcus dextrinicus and Pediococcus pentoxaceus.

The ribotype patterns of the seven strains shown in FIG. 2 fall into three RiboGroups. Two strains (#114 and #119) have identical ribotypes. One of these strains is a heterolactic strain (#119) while the other is a homolactic strain which produces racemic lactate (#114). The one D-lactate producing strain (#79) exhibited a ribotype pattern which was different from the other six. The remaining four strains (#90, 127, 132 and 140) were classified in the same RiboGroup and were considered to be likely to be identified to the same taxon level, despite the fact that their ribotype patterns were not identical. Of the four strains with a MIL 4–1132 pattern, three were L-lactate producing strains (#90, 132 and 140) while the fourth (#127) produced racemic lactate.

EXAMPLE 11

Effect of Added Base on Lactate Production

The effect of the additon of varying amounts of $CaCO_3$ on the lactate productivity of homolactic strain #41 was examined. The experiments were carried out at 47° C. in Medium A supplemented with 8 vol. % CSL, 200 g/L glucose, and varying amounts of added calcium carbonate (30–90 g/L). The results are shown in Table 9 below.

TABLE 9

Effect of $CaCO_3$ on Lactate Production

| $CaCO_3$ Conc. | Lactate Production (g/L) | | | | Final pH |
|---|---|---|---|---|---|
| | 0 hr. | 24 hr. | 51 hr. | 120 hr. | |
| 30 g/L | 3.17 | 48.1 | 75.5 | 75.7 | 3.98 |
| 40 g/L | 6.12 | 53.4 | 81.3 | 87.0 | 4.48 |
| 50 g/L | 5.84 | 49.4 | 83.4 | 88.1 | 4.73 |
| 60 g/L | 3.21 | 50.2 | 75.4 | 77.2 | 4.75 |
| 70 g/L | 4.85 | 48.9 | 75.3 | 73.8 | 4.8 |
| 80 g/L | 3.45 | 54.4 | 61.1 | 83.6 | 4.77 |
| 90 g/L | 5.39 | 49.6 | 57.8 | 83.6 | 4.74 |

EXAMPLE 12

Figure 3:
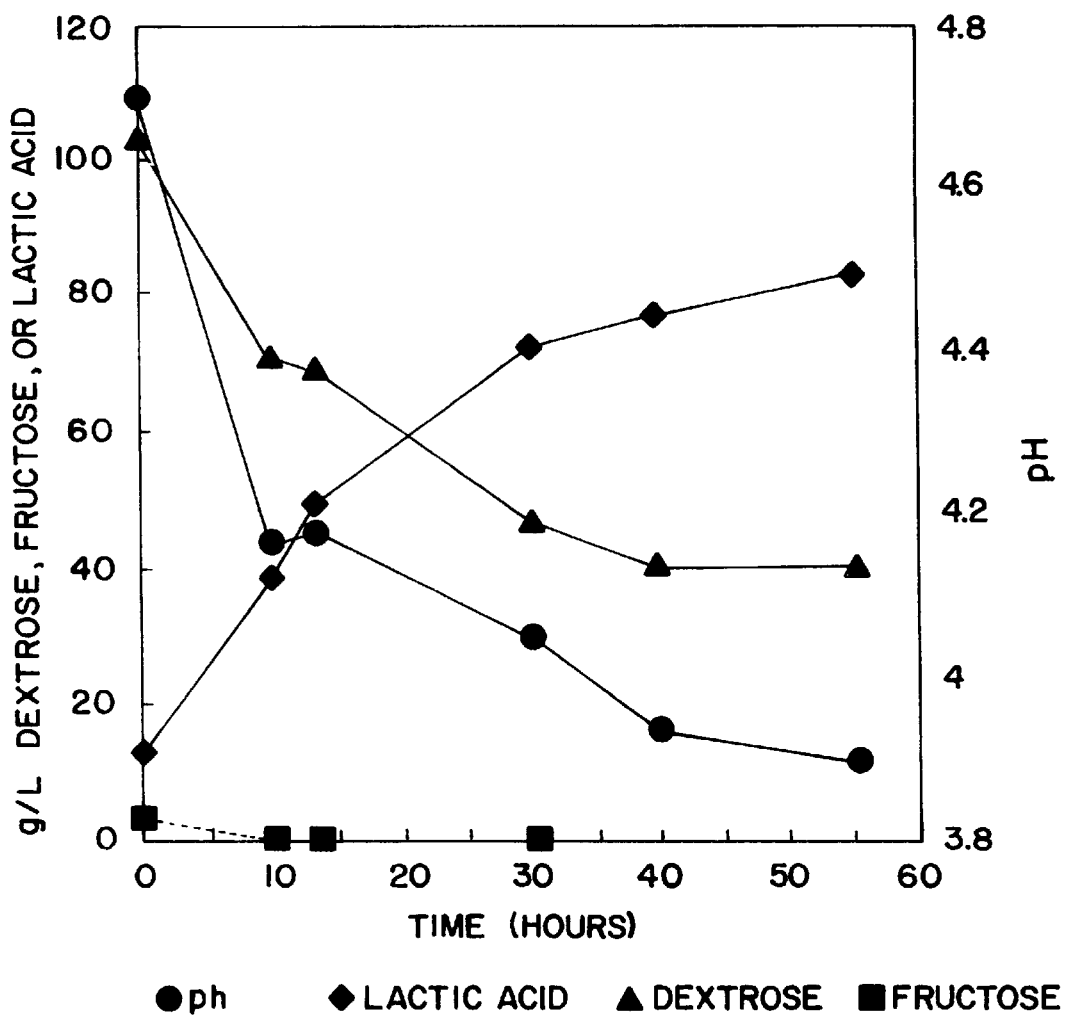
FIG. 3 is a graph showing the fermentation profile of glucose, fructose and lactate for incubation of strain #41 in a nutrient medium containing 10 vol. % corn steep liquor, 100 g/L glucose and 33.4 g/L calcium carbonate.

Fermentation Profile of Strain #41 with 12% CSL. 90 g/L Glucose and 33.4 g/L $CaCO_3$ FIG. 3 shows the profile of pH and the organic components in the fermentation broth as a function of time during the course of a representative fermentation experiment. The profile shown in FIG. 3 is based on results obtained from incubation at 47° C. of strain #41 in Medium B supplemented with 10 vol. % CSL, 100 g/L glucose and 33.4 g/L calcium carbonate.

EXAMPLE 13

Figure 4:
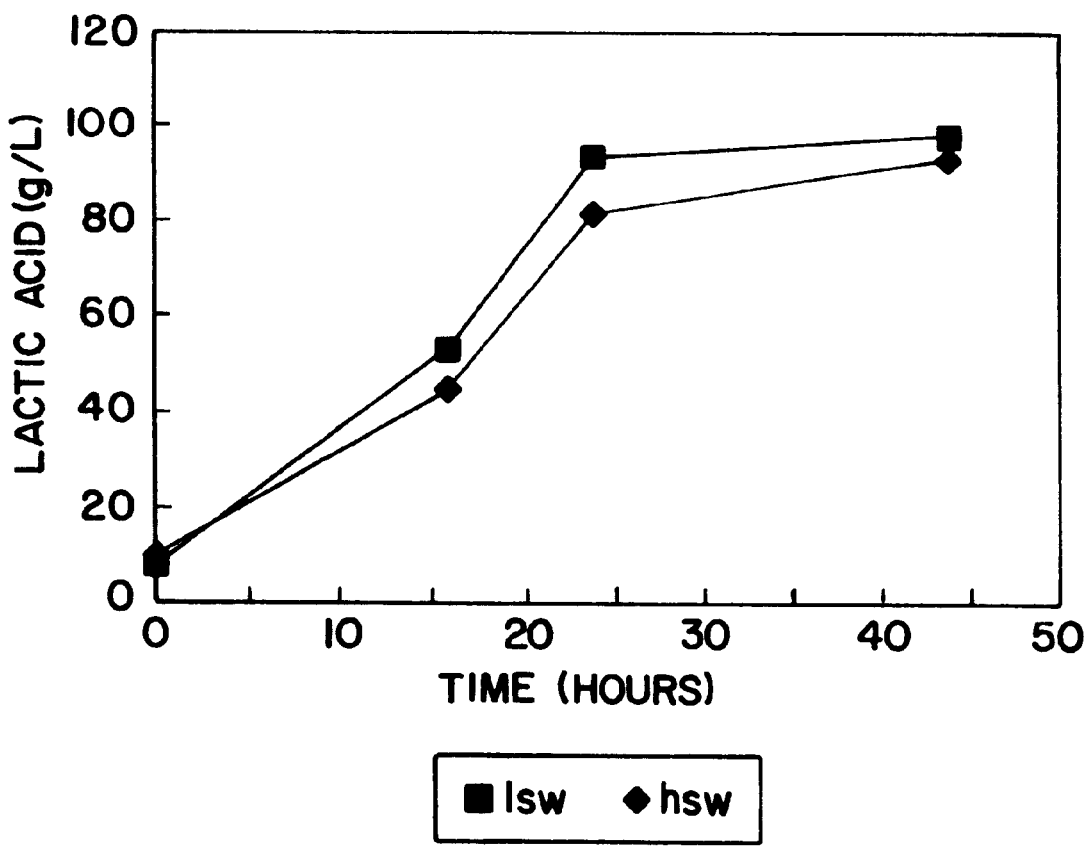
FIG. 4 is a graph showing lactate production from incubation of strain #41 in a nutrient medium containing 90 g/L glucose, 33.4 g/L calcium carbonate and either 12 vol. % corn steep liquor or 36 vol. % light steep water.

Fermentation Profile of Strain #41 with 90 g/L Glucose. 33.4 g/L $CaCO_3$ and 12% CSL/36% LSW FIG. 4 shows lactate production as a function of time during the course of representative fermentation experiments with strain #41. The fermentations were carried out using the procedure described in Example 1. The profile shown in FIG. 4 is based on results obtained from incubation of strain #41 at 47° C. in Medium C supplemented with 90 g/L glucose, 33.4 g/L calcium carbonate and either 12 vol. % CSL (36 wt. % dry solids) or 36 vol. % LSW (12 wt. % dry solids). The results summarized in Table 10 below show final free lactic acid levels of about 40 g/L free with either source of corn step water. Since the lactate was produced with an L-lactate producing strain (#41), at least about 35 g/L free L-lactic acid was present at the conclusion of these fermentations (the remainder is free D-lactate present in the added steep water).

TABLE 10

Lactate Production with Strain #41

| Lactate (g/L) | Corn Steep Water Source | |
|---|---|---|
| | 12% CSL | 36% LSW |
| 0 hrs. | 10.3 | 8.4 |
| 16 hrs. | 44.0 | 52.4 |
| 24 hrs. | 80.5 | 92.2 |
| 44 hrs. | 91.5 | 96.8 |
| Final pH | 3.92 | 3.98 |
| Final Free Lactate (g/L) | 42 | 41 |

EXAMPLE 14

Figure 5:
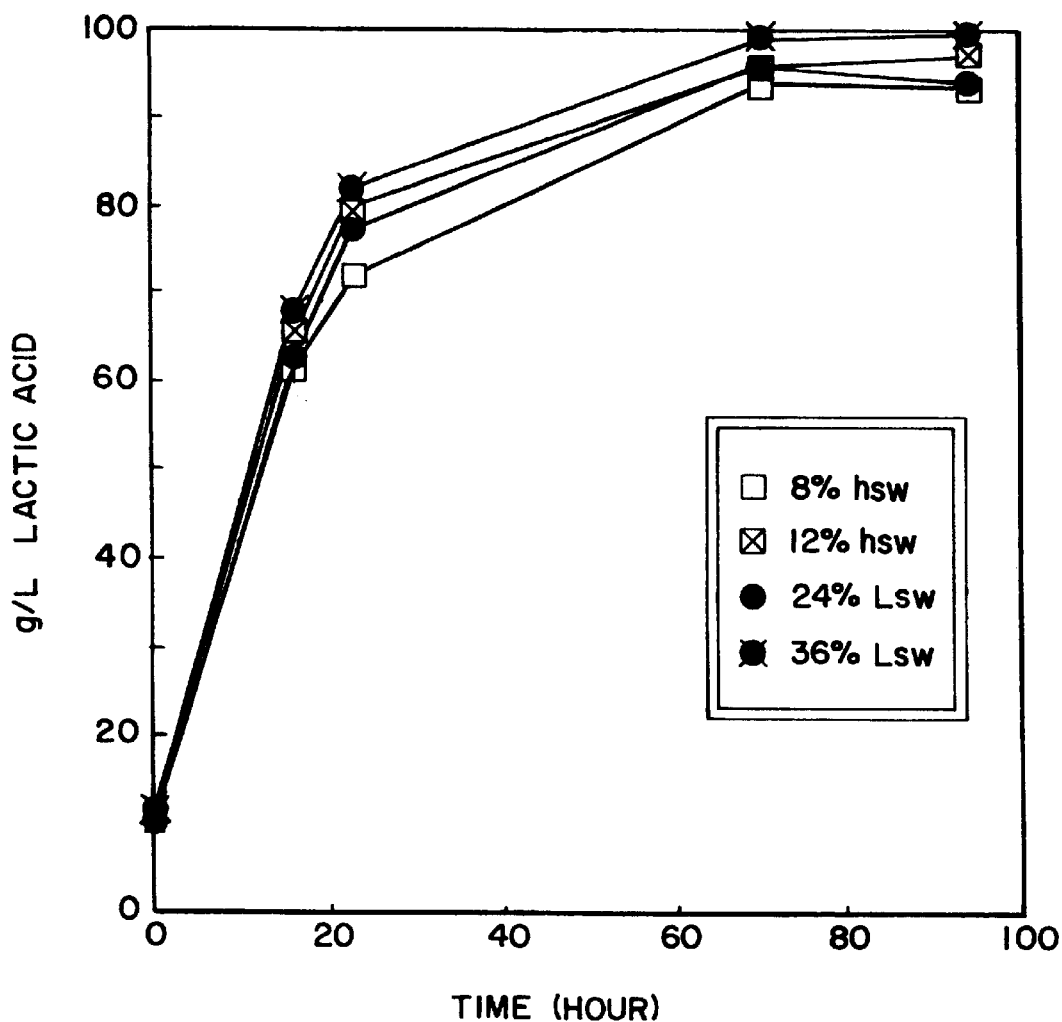
FIG. 5 is a graph showing the fermentation profile of glucose, fructose and lactate for incubation of homolactic strain #41 in a nutrient medium containing 90 g/L glucose, 36.6 g/L calcium carbonate and varying amounts of corn steep water.
Figure 6:
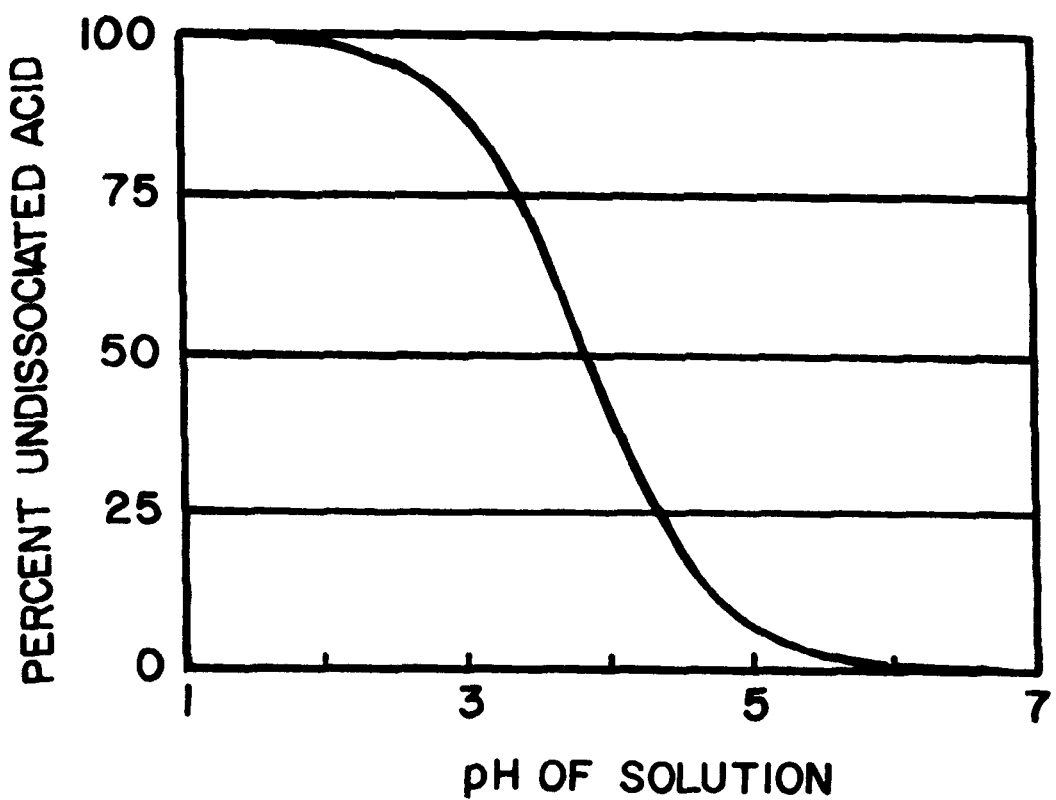
FIG. 6 is a graph showing the percentage undissociated lactic acid ("free lactic acid") as a function of pH.

Lactate Production of Strain 41 with 8–12% CSL, 90 g/L Glucose and 36.6 g/L $CaCO_3$ FIG. 5 shows lactate production as a function of time during the course of representative fermentation experiments with strain #41. The fermentations were carried out using a modified version of the procedure described in Example 1. Cells of strain #41 were pregrown in 800 ml of medium and then separated from the medium. The pregrown cells were then resuspended in 800 ml of fresh medium. The profile shown in FIG. 5 is based on results obtained from incubation of the pregrown cells at 47° C. in Medium B supplemented with 90 g/L glucose, 36.6 g/L calcium carbonate and either 8 vol. % CSL (36 wt. % dry solids), 12 vol. % CSL, 24 vol. % LSW (12 wt. % dry solids), or 36 vol. % LSW.

TABLE 11

Lactate Production with Strain #41

| Corn Steep Water Source | Final pH | Lactate | Free Lactic |
|---|---|---|---|
| 8% CSL | 3.83 | 93 g/L | 47 g/L |
| 24% LSW | 3.90 | 94 g/L | 44 g/L |
| 12% CSL | 3.80 | 97 g/L | 52 g/L |
| 36% LSW | 3.81 | 99.5 g/L | 53 g/L |

EXAMPLE 15

Effect of Added Glucose on Lactate Production

The effects varying the amounts of an added carbohydrate source (glucose) on lactate production was examined for the homolactic strain #41. The fermentations were run by incubating the #41 strain at 48° C. in Medium A supplemented with 10 vol. % CSL, 20 g/L $CaCO_3$ and the indicated level of glucose using the standard fermentation procedure described in Example 1. The medium also contained an additional 1–15 g/L fermentable sugar (mainly glucose and fructose) from the corn steep liquor. The results are shown in Table 12 below. The results of this experiment suggest that at least for the level of base added (20 g/L $CaCO_3$), lactate productivity may be enhanced by the addition of at least about 50 g/L of a carbohydrate source such as glucose.

TABLE X1

Effect of Glucose on Lactate Production

| | Lactate Production (g/L) | | |
|---|---|---|---|
| Glucose Added | 24 hr. | 48 hr. | 72 hr. |
| 30 g/L | 14 | 39 | 42 |
| 50 g/l | 11 | 51 | 55 |
| 80 g/L | 11 | 50 | 67 |
| 100 g/l | 9 | 47 | 65 |

The invention has been described with reference to various specific and preferred embodiments and techniques. The invention is not to be construed, however, as limited to the specific embodiments disclosed in the specification. It should be understood that many variations and modifications may be made while remaining within the spirit and scope of the invention.

TABLE 1

Isolated Homolactic Strains

| Strain No. | g/L Lactate | pH | % L-Lactate |
|---|---|---|---|
| 1 | 16.7 | 4.04 | 34 |
| 2 | 19.4 | 3.97 | 36 |
| 3 | | 4.51 | |
| 5 | 8.1 | 5.22 | 18 |
| 6 | 18.4 | 4.02 | 38 |
| 7 | 17.5 | 4.03 | 69 |
| 8 | 23.8 | 4.51 | 43 |
| 9 | 25.1 | 4.29 | 34 |
| 10 | 23.6 | 4.33 | 73 |
| 11 | 26.2 | 4.3 | 37 |
| 12 | 24.6 | 4.32 | 36 |
| 13 | 21.6 | 4.22 | 54 |
| 14 | 24.3 | 4.15 | 77 |
| 15 | 24.2 | 4.13 | 51 |
| 16 | 21.3 | 4.25 | 64 |
| 17 | 18.1 | 4.34 | 39 |
| 18 | 25.2 | 4.28 | 74 |
| 19 | 10.4 | 5.06 | 35 |
| 20 | 25.3 | 4.14 | 69 |
| 21 | 23.1 | 4.17 | 76 |
| 22 | 22.4 | 4.21 | 75 |
| 23 | 28.6 | 4.12 | 78 |
| 24 | 22.8 | 4.19 | 41 |
| 25 | 22.6 | 4.19 | 44 |
| 26 | 8.1 | | 17 |
| 27 | 23.7 | 4.19 | 48 |
| 28 | 22 | 4.21 | 44 |
| 29 | 21.1 | 4.18 | 51 |
| 30 | 23.6 | 4.15 | 47 |
| 32 | 20.4 | 4.15 | 46 |
| 34 | 19.5 | | 41 |
| 35 | | | 40 |
| 36 | | | 35 |
| 37 | | | 37 |
| 38 | | | 42 |
| 39 | | | 62 |
| 40 | | | 36 |
| 41 | 24.5 | 4.17 | 76 |
| 42 | 25.9 | 4.25 | 75 |
| 43 | 25 | 4.26 | 74 |
| 44 | 26.2 | 4.28 | 74 |
| 45 | 25.9 | 4.27 | 74 |
| 46 | 27.4 | 4.25 | 76 |
| 47 | 26 | 4.27 | 73 |
| 48 | 13.3 | 4.54 | 47 |
| 49 | 28.4 | 4.19 | 47 |
| 50 | 29.2 | 4.21 | 47 |
| 51 | 26.1 | 4.22 | 76 |
| 52 | 30.6 | | 48 |
| 55 | | | 2 |
| 56 | | | 31 |
| 57 | | | 32 |
| 58 | | | 0 |
| 59 | | | 0 |
| 60 | | | 0 |
| 61 | | | 45 |
| 62 | | | 88 |
| 63 | | | 5 |
| 64 | | | 92 |
| 65 | | | 41 |
| 66 | | | 4 |
| 67 | | | 5 |
| 68 | | | 5 |
| 69 | | | 49 |
| 70 | | | 48 |
| 71 | | | 44 |
| 72 | | | 5 |
| 73 | | | 5 |
| 74 | | | 5 |
| 75 | | | 3 |
| 76 | 53.27 | | 2 |
| 77 | | | 4 |
| 78 | | | 3 |
| 79 | | | 3 |
| 80 | | | 3 |
| 81 | 15.8 | | |
| 82 | 16.7 | | |
| 83 | 39.9 | | 55 |
| 84 | 14 | | |
| 85 | 14.2 | | |
| 86 | 8.1 | | |
| 87 | 8.4 | | |
| 88 | 46.1 | | 55 |

What is claimed is:

1. A process for producing lactic acid comprising:
   (a) incubating an acid-tolerant homolactic bacterial strain in nutrient medium at an incubation pH sufficient to allow production of lactic acid by the acid-tolerant homolactic bacterial stra in the nutrient medium, wherein the final incubation pH is pH 4.0 or less, and the step of incubating is provided at a temperature of at least about 30° C. to produce:
     (i) a solution including at least about 25 g/L free L-lactic acid or at least about 25 g/L free D-lactic acid;
     (ii) free lactic acid at an overall rate of at least about 1.0 g/L/hr; and
     (iii) the solution including at least about 25 g/L free L-lactic acid or at least about 25 g/L free D-lactic acid, wherein the free L-lactic acid is provided at an optical purity of at least about 50% or the free D-lactic acid is provided at an optical purity of at least about 50%; and
   (b) recovering free lactic acid.

2. The process of claim 1 comprising incubating the bacterial strain in the nutrient medium to produce a solution including at least about 40 g/L free L-lactic acid.

3. The process of claim 1 comprising incubating the bacterial strain at about 35° C. to about 53° C.

4. The process of claim 1 wherein the nutrient medium comprises at least about 15 g/L corn steep water dry solids.

5. The process of claim 1 wherein the nutrient medium comprises at least about 50 g/L carbohydrate.

6. The process of claim 1 wherein the nutrient medium comprises base.

7. The process of claim 1 wherein the nutrient medium comprises a lactate salt.

8. The process of claim 1 comprising incubating the bacterial strain at a temperature of at least about 47° C. to produce a solution containing at least about 40 g/L free L-lactic acid;

wherein the nutrient medium includes (i) at least about 25 g/L corn steep water dry solids, (ii) at least about 50 g/L glucose, or 50 g/L fructose, or 50 g/L of a mixture thereof, and (iii) at least about 20 g/L $CaCO_3$.

9. The process of claim 8, wherein the nutrient medium further comprises yeast extract.

10. The process of claim 8, wherein the nutrient medium further comprises nonionic surfactant.

11. The process of claim 6 wherein the base comprises calcium carbonate, sodium hydroxide, ammonium hydroxide, sodium bicarbonate or a mixture thereof.

12. The process of claim 7 wherein the lactate salt comprises calcium lactate, sodium lactate, ammonium lactate or a mixture thereof.

13. A process for producing lactic acid comprising:

(a) incubating an acid-tolerant homolactic bacterial strain in nutrient medium comprising corn steep water at an incubation pH sufficient to allow production of lactic acid by the acid-tolerant homolactic bacterial strain in the nutrient medium, wherein the final incubation pH is pH 4.2 or less, and the step of incubating is provided at a temperature of at least about 30° C. to produce:

(i) a solution having at least about 25 g/L free L-lactic acid or at least about 25 g/L free D-lactic acid; and (ii) the solution having at least about 25 g/L free L-lactic acid or at least about 25 g/L free D-lactic acid, wherein the free L-lactic acid is provided at an optical purity of at least about 80% or the free D-lactic acid is provided at an optical purity of at least about 80%;

(b) recovering free lactic acid.

14. The process of claim 13 wherein the acid-tolerant homolactic bacterial strain produces at least about 40 g/L free lactic acid.

15. The process of claim 13 wherein the acid-tolerant homolactic bacterial strain produces at least about 40 g/L free L-lactic acid at an incubation temperature above about 47° C.

16. The process of claim 13 wherein the nutrient medium comprises at least about 15 g/L corn steep water dry solids.

17. The process of claim 13, wherein base is not added during the step of incubating.

* * * * *

UNITED STATES PATENT AND TRADEMARK OFFICE
CERTIFICATE OF CORRECTION

PATENT NO. : 6,475,759 B1
DATED : November 5, 2002
INVENTOR(S) : Carlson et al.

It is certified that error appears in the above-identified patent and that said Letters Patent is hereby corrected as shown below:

Column 2,
Line 18, "generated by these recombinant" should read -- generated by these recombinant --

Column 6,
Line 28, "jsut" should read -- just --
Line 56, "howver" should read -- however --

Column 10,
Line 37, "recyled" should read -- recycled --
Line 57, "soild" should read -- solid --

Column 22,
Line 41, "bacterial stra in the" should read -- bacterial strain in the --

Signed and Sealed this

Eighth Day of April, 2003

JAMES E. ROGAN
*Director of the United States Patent and Trademark Office*